(12) United States Patent
Shiraishi et al.

(10) Patent No.: US 8,822,753 B2
(45) Date of Patent: Sep. 2, 2014

(54) ABSORBENT ARTICLE

(75) Inventors: Tsukasa Shiraishi, Kagawa (JP);
Yusuke Kawakami, Kagawa (JP)

(73) Assignee: Unicharm Corporation, Tokyo (JP)

( * ) Notice: Subject to any disclaimer, the term of this patent is extended or adjusted under 35 U.S.C. 154(b) by 374 days.

(21) Appl. No.: 12/990,291

(22) PCT Filed: Mar. 23, 2009

(86) PCT No.: PCT/JP2009/055578
§ 371 (c)(1),
(2), (4) Date: Dec. 13, 2010

(87) PCT Pub. No.: WO2009/133730
PCT Pub. Date: Nov. 5, 2009

(65) Prior Publication Data
US 2011/0112497 A1    May 12, 2011

(30) Foreign Application Priority Data
May 1, 2008   (JP) ................................. 2008-119992

(51) Int. Cl.
*A61F 13/15*   (2006.01)
*A61F 13/20*   (2006.01)
*A61F 13/42*   (2006.01)

(52) U.S. Cl.
CPC ..................................... *A61F 13/42* (2013.01)
USPC ....................................................... 604/361

(58) Field of Classification Search
USPC ....................................................... 604/361
See application file for complete search history.

(56) References Cited

U.S. PATENT DOCUMENTS

| 4,192,311 A | 3/1980 | Felfoldi |
| 4,507,121 A | 3/1985 | Leung |
| 5,354,289 A | 10/1994 | Mitchell et al. |
| 5,522,809 A * | 6/1996 | Larsonneur .................. 604/361 |
| 2006/0069361 A1* | 3/2006 | Olson ........................... 604/361 |
| 2008/0147030 A1* | 6/2008 | Nhan et al. ................... 604/361 |
| 2009/0157024 A1* | 6/2009 | Song ............................. 604/361 |

FOREIGN PATENT DOCUMENTS

| EP | 0 012 492 A1 | 6/1980 |
| FR | 2733146 A1 | 10/1996 |

(Continued)

OTHER PUBLICATIONS

International Search Report from corresponding PCT application No. PCT/JP2009-055578 dated Jun. 23, 2009, 4 pgs.

(Continued)

*Primary Examiner* — Melanie Hand
*Assistant Examiner* — Aundria Hairell
(74) *Attorney, Agent, or Firm* — Brinks Gilson & Lione (57) ABSTRACT

An absorbent article that enables the presence of moisture, for example, derived from urination to be easily recognized. The absorbent article includes an outer sheet provided on a side that faces a wearer's skin, i.e., on its side facing a liquid-absorbent structure with moisture visualizing elements. The moisture visualizing elements are formed by coating the outer sheet with hot melt composition comprising pH indicator mixed with pressure-sensitive adhesive ingredient. Two or more stripes of the hot melt composition forming the moisture visualizing elements extend in a longitudinal direction at least across a crotch region. Between the moisture visualizing elements and the liquid-absorbent structure, there is provided a barrier sheet or barrier sheets extending in a transverse direction so as to intersect the moisture visualizing elements comprising two or more stripes of the hot melt composition.

8 Claims, 5 Drawing Sheets

(56) References Cited

FOREIGN PATENT DOCUMENTS

| | | |
|---|---|---|
| JP | 11-004852 | 1/1999 |
| JP | 2004-236826 | 8/2004 |
| JP | 2005-021389 | 1/2005 |
| JP | 2007-175390 | 7/2007 |
| JP | 2007-236865 | 9/2007 |

OTHER PUBLICATIONS

European Search Report from corresponding EP application No. 09738667.6 dated Nov. 21, 2012 (5 pgs.).

* cited by examiner

ABSORBENT ARTICLE

RELATED APPLICATION

This application is a 35 U.S.C. §371 national phase filing of International Patent Application No. PCT/JP2009/055578, filed Mar. 23, 2009, through which and to which priority is claimed under 35 U.S.C. §119 to Japanese Patent Application No. 2008-119992, filed May 1, 2008.

TECHNICAL FIELD

The present invention relates to absorbent articles and more particularly to absorbent articles such as disposable diapers, toilet-training pants or incontinent briefs.

RELATED ART

Leak indicator means adapted to indicate whether urination has occurred or not in disposable diapers is known, for example, from JP 2004-236826 A (PATENT DOCUMENT 1). According to the disclosure of this PATENT DOCUMENT 1, the diaper comprises front and rear waist regions, a crotch region, an inner sheet facing the wearer's skin, an outer sheet facing a wearer's garment and an absorbent structure sandwiched between the inner and outer sheets. The outer sheet is provided on its side facing the absorbent structure with the leak indicator means. The leak indicator means is formed by water-soluble ink adapted to become invisible upon contact with moisture such as urine or to develop color change.
[PATENT DOCUMENT 1] JP 2004-236826 A

DISCLOSURE OF THE INVENTION

Problem to be Solved by the Invention

When the amount of urination is relatively small or the frequency of urination is relatively low, the leak indicator means becomes partially invisible or develops color change, i.e., the leak indicator partially remains unchanged. In other words, the portions of the leak indicator means which has developed a change can be compared with the portions of the leak indicator means remaining unchanged and thereby it can be easily determined whether urination has occurred or not. However, if the amount of urination is relatively large, the leak indicator means will fully become invisible or develop color change, making it impossible to compare the leak indicator means before such change occurs with the leak indicator means after such change has occurred. In other words, a problem has been left unsolved that it will be impossible to determine whether urination has occurred or not unless optical characteristic such as color is kept in mind.

It is an object of the present invention to provide an absorbent article enabling the presence of moisture, for example, derived from urination to be easily recognized.

Measure to Solve the Problem

The object set forth above is achieved, according to the present invention, by an improvement in an absorbent article having a longitudinal direction, a transverse direction, aside facing the wearer's skin, a side facing a wearer's garment, a front waist region, a rear waist region and a crotch region extending between the front and rear waist regions wherein these regions are contiguous one to another in the longitudinal direction, and comprising an inner sheet lying on the side facing wearer's skin, an outer sheet lying on the side facing wearer's garment, a liquid-absorbent structure sandwiched between the inner and outer sheets and occupying at least the crotch region and moisture visualizing elements formed on a side of the outer sheet facing the liquid-absorbent structure and adapted to develop change of optical effect upon contact with moisture.

The improvement according to the present invention is characterized in that a barrier sheet of moisture-impervious is provided between the moisture visualizing elements and the liquid-absorbent structure so as to overlap a part of the moisture visualizing elements and thereby to restrain the moisture having been absorbed by the liquid-absorbent structure from coming in direct contact with the overlapped part of the moisture visualizing elements.

According to one preferred embodiment, the barrier sheet is provided in the crotch region aside toward the front waist region.

According to another preferred embodiment, the barrier sheet comprises a pair of sheet slips spaced from each other in the transverse direction.

According to still another preferred embodiment, the barrier sheet is placed so that a transverse middle of the barrier sheet coincides with a longitudinal center line bisecting a dimension of the absorbent article in the transverse direction.

According to yet another preferred embodiment, the barrier sheet has a length dimension of 10 mm or longer as measured in the transverse direction.

Effect of the Invention

According to the present invention, a moisture-impervious barrier sheet is provided between said moisture visualizing elements and said liquid-absorbent structure so as to overlap a part of said moisture visualizing elements and thereby to define portions of the moisture visualizing elements which are free from contact with moisture. In these portions free from contact with moisture, substantially no change of the optical effect and therefore these portions can be used as a reference to compare the remaining portions of the moisture visualizing elements after contact with moisture with those before contact with moisture. In this way, any change of the optical effect developed by the moisture visualizing elements can be easily recognized.

According to the embodiment wherein the barrier sheet is provided in said crotch region aside toward said front waist region, urine (i.e., moisture) is normally discharged onto the spot in the crotch region put aside toward the front waist region in the upright posture on the assumption that the absorbent article is a diaper. Thus, the placement of the barrier sheet coincides with the spot onto which urine is discharged and even a relatively small amount of urination can be reliably recognized.

According to the embodiment wherein the barrier sheet comprises a pair of sheet slips spaced from each other in the transverse direction, urine discharged onto a spot in the vicinity of the longitudinal center line bisecting the dimension of the absorbent article in the transverse direction comes in contact with the moisture visualizing elements. In consequence, it can be reliably determined whether urination has occurred or not.

The barrier sheet is placed so that the transverse middle of the barrier sheet coincides with the longitudinal center line bisecting a dimension of the absorbent article in the transverse direction. With such arrangement, even if the amount of urine discharged onto the spot in the vicinity of the longitudinal center line becomes gradually smaller with distance from the longitudinal center line and color change developed by the moisture visualizing elements becomes correspondingly unremarkable, the color change is reliably developed around the barrier sheet. Therefore it is easy to compare the color change with the color unchangeable portions overlapped by the barrier sheet. This means that urination can be recognized even if the amount of urination is relatively small.

Dimensioning the length dimension of the barrier sheet to 10 mm or longer as measured in the transverse direction is effective to constrain permeation of moisture into the barrier sheet from the periphery thereof and to constrain the portions overlapped by the barrier sheet from developing color change particularly immediately after urination.

IDENTIFICATION OF REFERENCE NUMERALS USED IN THE DRAWINGS 1 diaper
5 front waist region
6 rear waist region
7 crotch region
8 inner sheet
9 outer sheet
10 liquid-absorbent structure
21 moisture visualizing element
22 barrier sheet
23 sheet slip

DETAILED DESCRIPTION OF THE PREFERRED EMBODIMENTS

Details of the present invention will be more fully understood from the following exemplary description given hereunder with respect to a disposable diaper as an embodiment of an absorbent article.
<First Embodiment>

Figure 1:
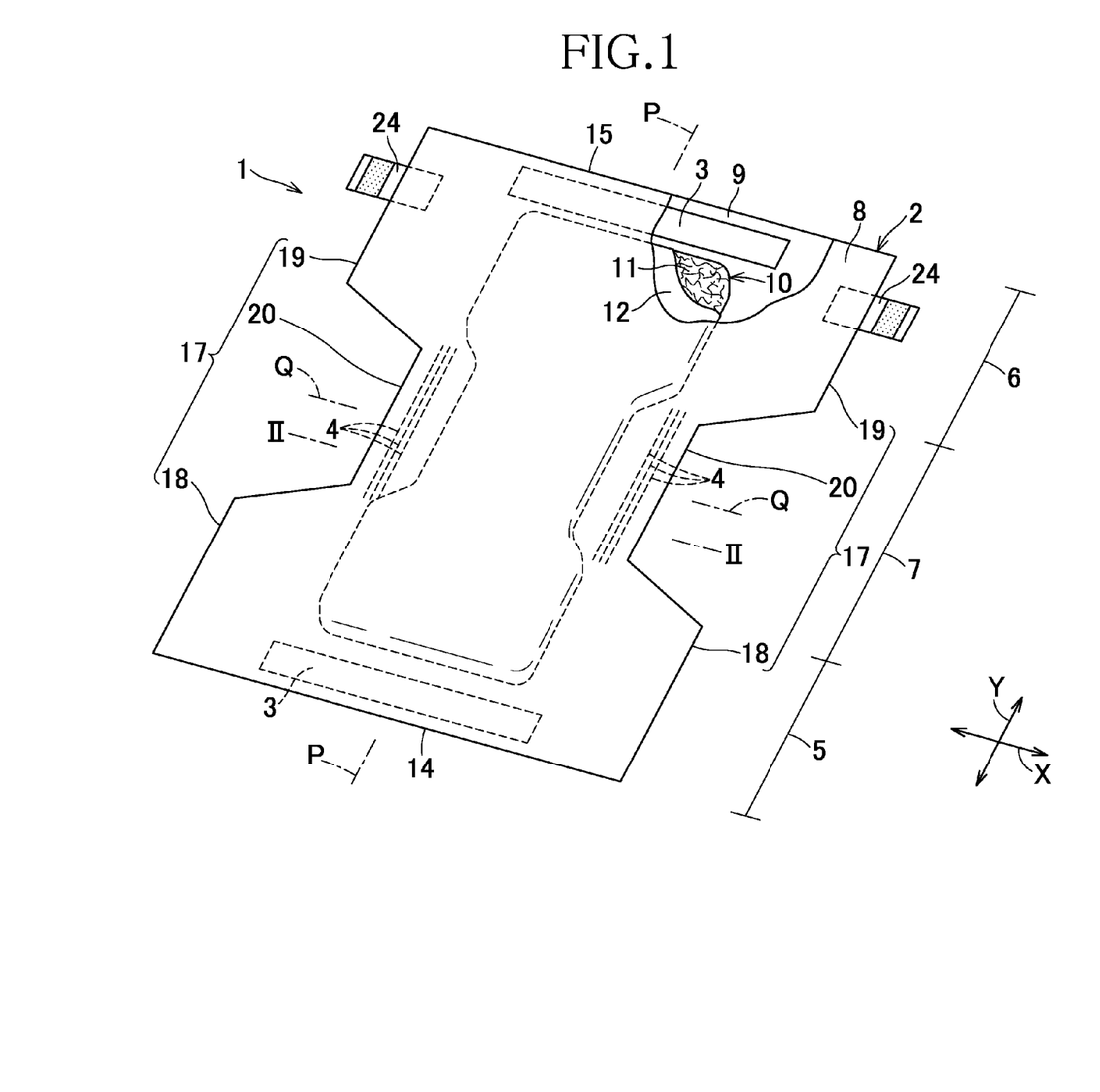
[FIG. 1] Plan view of a diaper according to a first embodiment.
Figure 2:
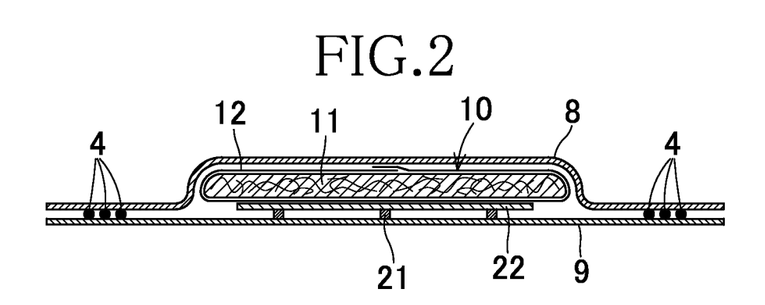
[FIG. 2] Sectional view taken along the line II-II in FIG. 1.
Figure 3:
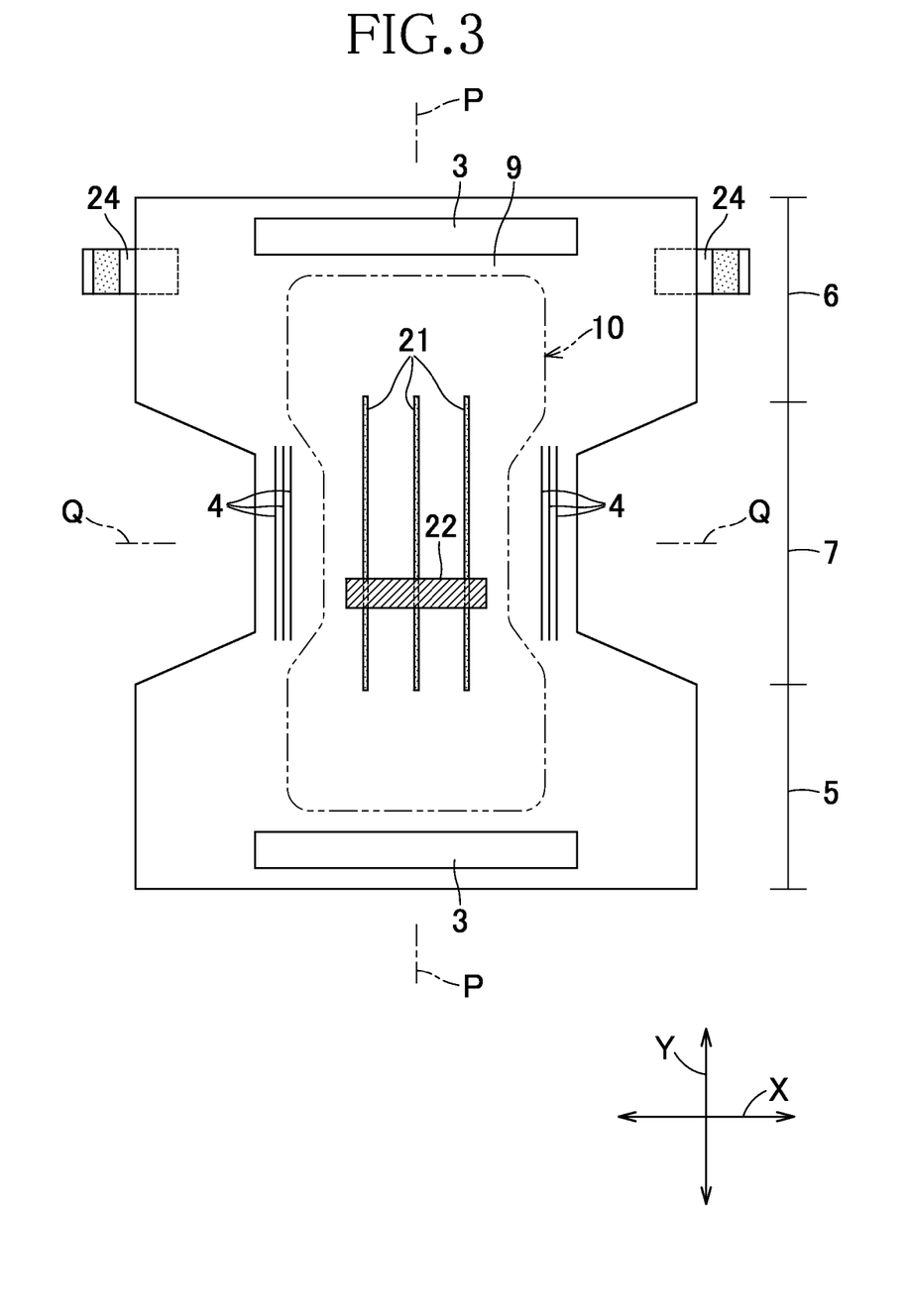
[FIG. 3] Plan view corresponding to FIG. 1 an inner sheet and a liquid-absorbent structure eliminated therefrom.

FIGS. 1 through 3 illustrate a first embodiment of the invention wherein respective elastic members are shown as elasticity thereof being inactivated. FIG. 1 is a plan view showing a diaper 1 of so-called open-type flatly developed and partially cutaway for inconvenience of illustration and FIG. 2 is a sectional view taken along the line II-II in FIG. 1. As illustrated, the diaper 1 comprises a chassis 2, waist elastic members 3 and leg elastic members 4. The chassis 2 comprises a front waist region 5, a rear waist region 6 and a crotch region 7 extending between the front and rear waist regions 5, 6, these regions 5, 6 and 7 being contiguous one to another in a longitudinal direction Y. The chassis 2 includes a liquid-pervious inner sheet 8 defining an inner side facing the wearer's skin and a liquid-impervious outer sheet 9 defining an outer side facing the wearer's garment. The chassis 2 is provided between these inner and outer sheets 8, 9 with a liquid-absorbent structure 10 at least occupying the crotch region 7. The liquid-absorbent structure 10 comprises a liquid-absorbent core 11 formed, for example, by fluff pulp and a dispersant sheet 12 such as tissue paper with which the liquid-absorbent core 11 is wrapped.

The chassis 2 has front and rear ends 14, 15 opposed to each other in the longitudinal direction Y and extending in a transverse direction X along which respective waist elastic members 3 are attached to the chassis 2. Each of these waist-surrounding elastic members 3 is formed by an elasticized sheet attached to the chassis 2 under tension in the transverse direction X.

The chassis 2 has a pair of side edges 17 opposed to each other in the transverse direction X and extending in the longitudinal direction Y. Each of these side edges 17 comprises a front side edge 18 extending in the front waist region 5, a rear side edge 19 extending in the rear waist region 6 and a leg side edge 20 extending in the crotch region 7. The opposite side edges 17 describe curvatures along the respective leg side edges 20 which are convex toward a longitudinal center line P-P bisecting a dimension of the diaper 1 in the transverse direction X so that the chassis 2 as a whole has a concaved-shape.

The opposite side edges 17 are provided with a plurality of leg elastic members 4 extending along the leg side edges 20. Specifically, these leg elastic members 4 are attached to the chassis 2 under tension so as to be sandwiched between the inner and outer sheets 8, 9. The leg elastic members 4 bias the leg side edges 20 to fit around the wearer's legs and thereby prevent body waste such as urine from leaking beyond the leg side edges 20. The rear side edges 19 are provided on the side of the outer sheet 9 with fastener members 24 extending outward in the transverse direction 9 so that these fastener members 24 are engaged with the outer sheet 9 in the front waist region 5 to put the diaper 1 on the wearer's body.

FIG. 3 is a plan view corresponding to FIG. 1 with the inner sheet 8 and the liquid-absorbent structure 10 eliminated therefrom. As will be apparent from FIG. 3, a moisture visualizing element 21 is provided on the side of the outer sheet 9 facing the wearer's skin, i.e., facing the liquid-absorbent structure 10. The moisture visualizing element 21 is formed by coating the outer sheet 9 with hot melt composition comprising pressure-sensitive adhesive ingredient mixed with pH indicator. The moisture visualizing element 21 formed in this manner develops a color change upon contact with moisture and thereby visualizes the presence of moisture through such change of color. Two or more stripes each forming the moisture visualizing element 21 extend in the longitudinal direction Y at least across the crotch region 7. In this first embodiment, these moisture visualizing elements 21 extend across the crotch region 7 further into the front and rear waist regions 5, 6.

There is provided a barrier sheet 22 between the moisture visualizing elements 21 and the liquid-absorbent structure 10. The barrier sheet 22 extends in the transverse direction X across a plurality of the moisture visualizing elements 21 arranged so as to be spaced one from another in the transverse direction X. The barrier sheet 22 has a dimension of about 10 mm in the longitudinal direction Y and is set in the crotch region 7 put aside from a transverse center line Q-Q toward the front waist region 5. The barrier sheet 22 is bonded to at least one of the outer sheet 9 and the liquid-absorbent structure 10. The barrier sheet 22 is formed by hydrophobic fibrous nonwoven fabric and therefore spots of the respective moisture visualizing elements 21 overlapped by the barrier sheet 22 are prevented from contacting with moisture deriving from urination.

Upon urination by the user wearing the diaper 1 composed as has been described, urine passes through the inner sheet 8 and is absorbed by the liquid-absorbent structure 10. Then a portion of urine absorbed by the liquid-absorbent structure 10 comes in contact with the moisture visualizing elements 21. Upon contact urine, the moisture visualizing elements 21 develop change of color. The moisture visualizing elements 21 are adapted to be visible through the outer sheet 9 and, if the wearer is a baby, a helper or a parent of this baby can perceive that urination has occurred by observing such change of color.

The barrier sheet 22 is provided between the moisture visualizing elements 21 and the liquid-absorbent structure 10 and the portions of the moisture visualizing elements 21 overlapped by the barrier sheet 22 develop substantially no change of color even if urination occurs. With this unique arrangement, even if a large quantity of urine is discharged or urination occurs more than once and substantially most part of the moisture visualizing elements 21 come in contact with urine, no change of color is developed in the portions of the moisture visualizing elements 21 overlapped by the barrier sheet 22. Clear contrast with these portions developing no change of color, color change developing in remaining most part of the moisture visualizing element 21 can be easily recognized. If the portions developing no change of color are not provided, it would be very difficult for the helper or the parent to determine whether all the moisture visualizing elements have changed color or not unless the helper or the parent previously stores the initial color of these moisture visualizing elements 21 in his or her memory.

According to this first embodiment, the moisture visualizing elements 21 are formed in the crotch region 7 put aside from the transverse center line Q-Q toward the front waist region 5 and the middle one of these moisture visualizing element 21 lies on the longitudinal center line P-P. In other words, the moisture visualizing elements are positioned so as to be aligned with wearer's urethral orifice and the vicinity thereof. Consequently, even when a voided volume is insufficient for all the moisture visualizing elements to develop change of color and an amount of color change gradually decreases toward the front and rear waist regions 5, 6, change of color reliably develops in the moisture visualizing elements around the wearer's urethral orifice in a clear contrast with the portions overlapped by the barrier sheet 22. In this way, even if the amount of color change developed in the moisture visualizing elements 21 gradually decrease in a gradation mode, it is easy for the helper or the parent to determine whether urination has occurred or not.

While the dimension of the barrier sheet 22 in the longitudinal direction Y is 10 mm in this first embodiment, the invention is not limited to this. It should be understood here that the barrier sheet 22 dimensioned to be less than 10 mm in the longitudinal direction Y will unacceptably lessen the color unchangeable portions of the moisture visualizing elements 21, making it difficult to compare these portions with the color changed portions. In addition, the barrier sheet 22 might be soaked with urine seeping beyond peripheral edges of the barrier sheet 22 and the color unchangeable portions of the moisture visualizing elements might develop change of color. Taking account of this, it is rather preferably to dimension the barrier sheet 22 in the longitudinal direction Y relatively large and thereby to broaden the total area overlapping the moisture visualizing elements 21. By dimensioning the barrier sheet 22 in this manner, the portions of the moisture visualizing elements 21 overlapped by the barrier sheet 22 can be maintained color unchangeable for a long period against urine tends to seep into the portions of the barrier sheet 22 overlapping the moisture visualizing elements 21 and facilitate to compare these portions with the color changed portions.

However, if the barrier sheet 22 completely covers the moisture visualizing elements 21, no portion of the moisture visualizing elements 21 will be direct in contact with moisture. It is essential for the intended cooperation of the moisture visualizing elements 21 with the barrier sheet 22 that these two components should overlap each other not completely but partially. A basis weight of the barrier sheet 22 may be in a range of 10 to 30 g/m$^2$ and preferably in a range of 18 to 20 g/m$^2$. Excessively high basis weight leads to excessively high stiffness. Consequentially, the wearer might experience an incompatible feeling to wear, on one hand, and a joint effect between the barrier sheet 22 and the outer sheet 9 or the liquid-absorbent structure 10 might become unreliable, on the other hand. While the first embodiment uses a hydrophobic nonwoven fabric as the barrier sheet 22, it is also possible to use a hydrophobic film or the like as the barrier sheet 22.

While this embodiment uses hot melt composition comprising pressure-sensitive adhesive ingredient and pH indicator mixed therewith as the moisture visualizing elements, the present invention is not limited to this and any other composition can be used as the moisture visualizing elements 21 so far as color development, color fade or color change occurs upon contact with moisture to suggest the presence of moisture. Instead of using the hot melt composition, it is also possible to print the moisture visualizing elements directly on the diaper 1 with appropriate ink or to interpose the moisture visualizing elements in the form of a separately prepared sheet.

<Second Embodiment>

Figure 4:
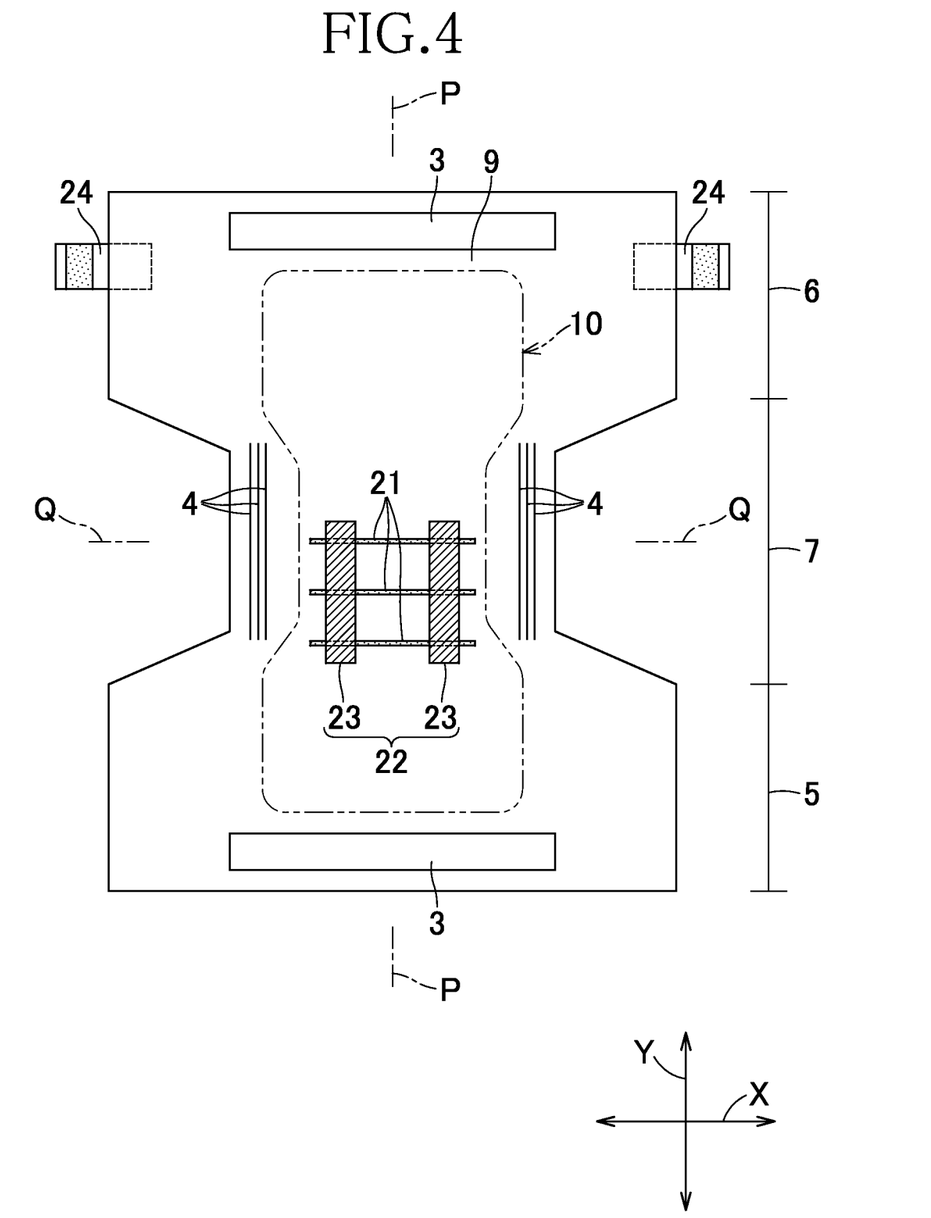
[FIG. 4] View similar to FIG. 3, showing a second embodiment.

FIG. 4 illustrates a second embodiment of the invention. This second embodiment is similar to the first embodiment except the position at which the moisture visualizing elements are formed and the position at which the barrier sheet is attached to the diaper 1. The components corresponding to those in the first embodiment are designated with the reference numerals common to the first embodiment and details of these common components will not be described.

In this embodiment also, a hot melt composition comprising pressure-sensitive adhesive ingredient and pH indicator mixed therewith is used as the moisture visualizing elements 21. As will be apparent from FIG. 4, the moisture visualizing elements 21 are formed by two or more stripes of hot melt composition extending in the transverse direction X with which the side of the outer sheet 9 is coated. As for placement of these moisture visualizing elements 21 are formed in the crotch region 7 put aside from the transverse center line Q-Q toward the front waist region 5.

The barrier sheet 22 is provided between the moisture visualizing elements 21 and the liquid-absorbent structure 10. The barrier sheet 22 comprises a pair of sheet slips 23 spaced from each other in the transverse direction X and extending in the longitudinal direction Y. These sheet slips 23 are attached to the diaper 1 symmetrically about the longitudinal center line P-P across the stripes of hot melt composition which is aligned in the longitudinal direction Y. A dimension of the sheet slip 23 in the transverse direction X is about 10 mm.

According to this second embodiment, the moisture visualizing elements 21 are formed in the crotch region 7 put aside toward the front waist region 5, i.e., substantially in alignment with the wearer's urethral orifice to ensure that the helper or the parent can reliably realize occurrence of urination. The sheet slips 23 are spaced from each other in the transverse direction X so as to intersect with, i.e., to overlap the moisture visualizing elements 21. This means that the barrier sheet 22 is not present in the vicinity of the longitudinal center line P-P on which urination occurs and, in consequence, even a small amount of urination reliably causes the moisture visualizing elements 21 to develop sufficient change of color to recognize occurrence of urination. Such change of color may be compared with color of the barrier sheets 22 provided on both sides of the center line P-P to facilitate determination whether urination has occurred or not.

<Third Embodiment>

Figure 5:
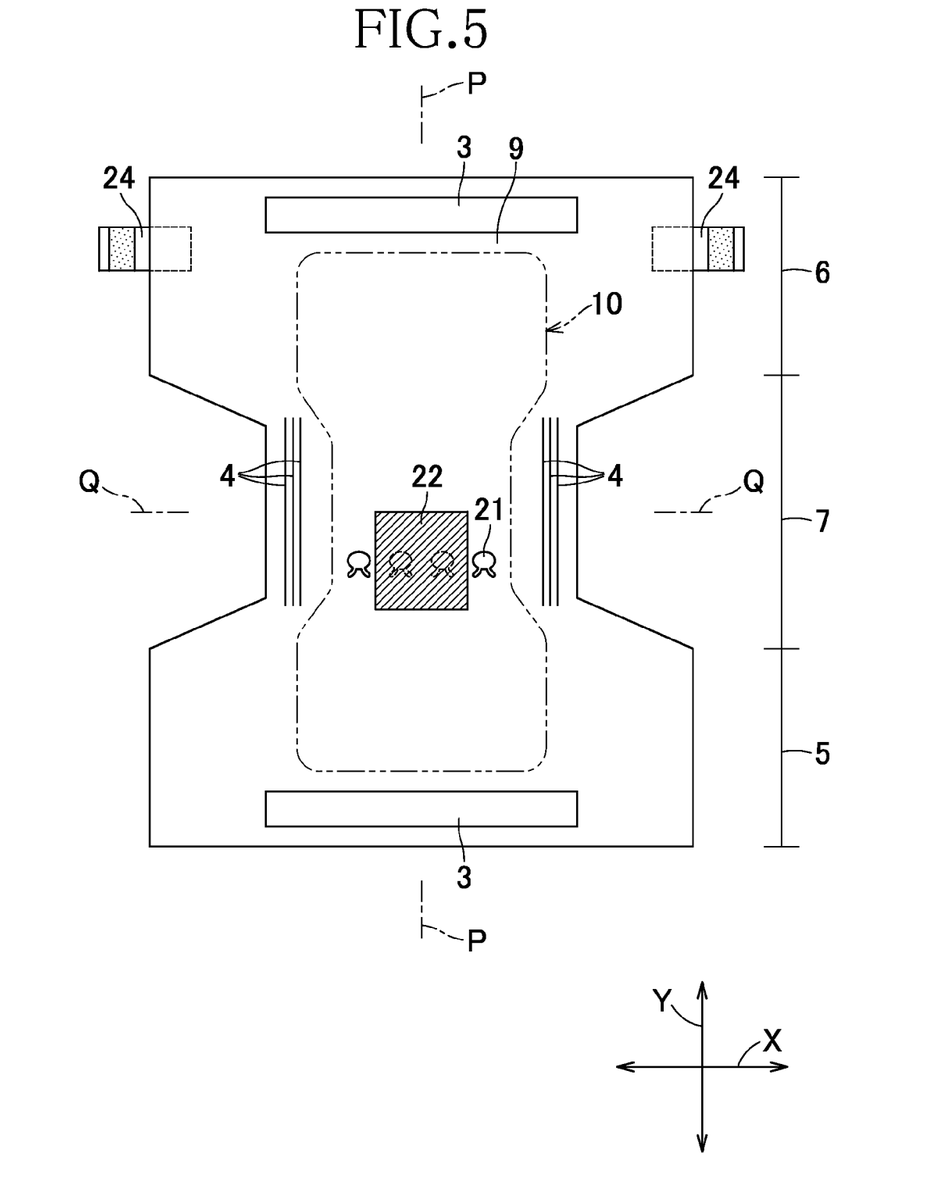
[FIG. 5] View similar to FIG. 4, showing a third embodiment.

FIG. 5 illustrates a third embodiment of the invention. This third embodiment is characterized in that the moisture visualizing elements 21 are formed by graphics. The components corresponding to those in the first embodiment are designated with the reference numerals common to the first embodiment and details of these common components will not be described. As will be apparent from FIG. 5, the moisture visualizing elements 21 are provided on the outer sheet 9 and these moisture visualizing elements 21 are formed by hot melt composition comprising pressure-sensitive adhesive ingredient and pH indicator mixed therewith. More specifically, the moisture visualizing elements 21 are defined by graphics printed with the hot melt composition and placed in the crotch region 7 put aside toward the front waist region 5. The graphics are intermittently arranged in the transverse direction X.

Between the moisture visualizing elements 21 and the liquid-absorbent structure 10, there is provided the barrier sheet 22 so as to overlap a part of the moisture visualizing elements 21 and to have its transverse middle coinciding with the longitudinal center line P-P. More specifically, the barrier sheet 22 overlaps some of the moisture visualizing elements 21 spaced one from another and not the remaining moisture visualizing elements 21 so that the color changed graphics and the color unchanged graphics would appear or some of the moisture visualizing elements 21 would become visible but the other moisture visualizing elements 21 would remain invisible. It can be facilitated thereby to determine whether moisture is present or not. In this case, the area of the barrier sheet 22 may be appropriately dimensioned so that the barrier sheet 22 would overlap some of the individual graphics.

Upon contact of the moisture with the moisture visualizing elements 21, the graphics develop change of color or partially fade away and partially make appearance, making it possible to determine whether moisture is present or not. It is also possible to create a kind of plot from a combination of the individual graphics before and after such change due to contact with moisture.

The invention claimed is:

1. An absorbent article comprising:
a longitudinal direction;
a transverse direction;
a side facing the wearer's skin;
a side facing a wearer's garment;
a front waist region;
a rear waist region and a crotch region extending between said front and rear waist regions wherein said front and rear waist regions and said crotch region are contiguous one to another in said longitudinal direction;
an inner sheet lying on said side facing the wearer's skin;
a liquid-impervious outer sheet lying on said side facing a wearer's garment;
a liquid-absorbent structure sandwiched between said inner and outer sheets and occupying at least said crotch region;
a plurality of moisture visualizing elements formed on a side of said outer sheet facing said liquid-absorbent structure and adapted to develop change of optical effect upon contact with moisture, said plurality of moisture visualizing elements extending in the longitudinal direction at least across the crotch region so as to enable detection of moisture across the crotch region, said plurality of moisture visualizing elements formed by coating portions of the outer sheet with a hot melt composition that comprises a pressure-sensitive adhesive ingredient mixed with a pH indicator; and
a barrier sheet of moisture-impervious provided between said plurality of moisture visualizing elements and said liquid-absorbent structure so as to overlap a part of said plurality of moisture visualizing elements and thereby to restrain the moisture having been absorbed by said liquid-absorbent structure from coming in direct contact with said part of said plurality of moisture visualizing elements, said barrier sheet comprising one of a hydrophobic nonwoven fabric and a hydrophobic film,
wherein the plurality of moisture visualizing elements extend outward from both side edges of the barrier sheet in the crotch region.

2. The absorbent article according to claim 1, wherein said barrier sheet is provided in said crotch region aside toward said front waist region.

3. The absorbent article according to claim 1, wherein said barrier sheet comprises a pair of sheet slips spaced from each other in said transverse direction.

4. The absorbent article according to claim 1, wherein said barrier sheet is placed so that a transverse middle of said barrier sheet coincides with a longitudinal center line bisecting a dimension of said absorbent article in said transverse direction.

5. The absorbent article according to claim 1, wherein said barrier sheet has a length dimension of 10 mm or longer as measured in said transverse direction.

6. The absorbent article according to claim 2, wherein said barrier sheet has a length dimension of 10 mm or longer as measured in said transverse direction.

7. The absorbent article according to claim 3, wherein said barrier sheet has a length dimension of 10 mm or longer as measured in said transverse direction.

8. The absorbent article according to claim 4, wherein said barrier sheet has a length dimension of 10 mm or longer as measured in said transverse direction.

* * * * *